US009956164B2

(12) United States Patent
Zaremba et al.

(10) Patent No.: US 9,956,164 B2
(45) Date of Patent: May 1, 2018

(54) VETERINARY PHARMACEUTICAL COMPOSITION AND USE THEREOF (71) Applicant: Veyx-Pharma GmbH, Schwarzenborn (DE)

(72) Inventors: Wolfgang Zaremba, Homberg (DE); Johannes Kauffold, Leipzig (DE); Wolfgang Friess, Iffeldorf (DE); Kerstin Hoffmann, Munich (DE); Yordanka Yordanova, Munich (DE)

(73) Assignee: Veyx-Pharma GmbH, Schwarzenborn (DE)

( * ) Notice: Subject to any disclaimer, the term of this patent is extended or adjusted under 35 U.S.C. 154(b) by 0 days. days.

(21) Appl. No.: 15/304,677

(22) PCT Filed: Apr. 16, 2015

(86) PCT No.: PCT/EP2015/058265
§ 371 (c)(1),
(2) Date: Dec. 29, 2016

(87) PCT Pub. No.: WO2015/158823
PCT Pub. Date: Oct. 22, 2015

(65) Prior Publication Data
US 2017/0189328 A1 Jul. 6, 2017

(30) Foreign Application Priority Data
Apr. 16, 2014 (DE) .................. 10 2014 207 353

(51) Int. Cl.
A61K 9/00 (2006.01)
A61K 38/24 (2006.01)

(52) U.S. Cl.
CPC ............ A61K 9/0002 (2013.01); A61K 38/24 (2013.01)

(58) Field of Classification Search
CPC ........ A61K 38/01; A61K 38/00; A61K 38/24; A61K 9/0002; A61K 9/1629; A61K 9/1652; A61K 9/1676; A61K 9/5026; A61K 9/5078; A61K 31/4709; A61K 31/522; A61K 38/09; A61K 47/14; A61K 47/44; A61K 9/0019; A61K 9/0024; A61K 9/10; A61K 9/148; A61L 2300/254; A61L 2300/412; A61L 2300/432; A61L 2430/02; A61L 2430/06; A61L 27/227; A61L 27/3608; A61L 27/365; A61L 27/3654; A61L 27/3683; A61L 27/3687; A61L 27/3847; A61L 27/3852; A61L 27/54
See application file for complete search history.

(56) References Cited

U.S. PATENT DOCUMENTS

| | | |
|---|---|---|
| 3,869,549 A | 3/1975 | Geller |
| 4,675,189 A | 6/1987 | Kent et al. |
| 4,764,378 A | 8/1988 | Keith et al. |
| 4,767,628 A | 8/1988 | Hutchinson |
| 4,835,139 A | 5/1989 | Tice et al. |
| 5,480,868 A | 1/1996 | Kamei et al. |
| 5,500,228 A | 3/1996 | Lawter et al. |
| 5,503,851 A | 4/1996 | Mank et al. |
| 5,536,508 A | 7/1996 | Canal et al. |
| 5,594,091 A | 1/1997 | Igari et al. |
| 5,736,151 A | 4/1998 | Foster et al. |
| 5,766,627 A | 6/1998 | Sankaram et al. |
| 5,851,451 A | 12/1998 | Takechi et al. |
| 6,051,558 A | 4/2000 | Burns et al. |
| 6,117,455 A | 9/2000 | Takada et al. |
| 6,245,346 B1 | 6/2001 | Rothen-Weinhold et al. |
| 6,245,740 B1 | 6/2001 | Goldenberg et al. |
| 6,270,001 B1 | 8/2001 | Tadic et al. |
| 6,287,588 B1 | 9/2001 | Shih et al. |
| 6,719,990 B2 | 4/2004 | Patel et al. |
| 6,777,386 B2 | 8/2004 | Trigg et al. |
| 7,105,487 B2 | 9/2006 | Zaremba et al. |
| 7,429,559 B2 | 9/2008 | Yamamoto et al. |
| 7,659,061 B2 | 2/2010 | Hendl et al. |
| 7,906,136 B2 | 3/2011 | Wong et al. |
| 8,088,726 B2 | 1/2012 | Yamamoto et al. |
| 8,092,830 B2 | 1/2012 | Yamamoto et al. |
| 8,921,326 B2 | 12/2014 | Futo et al. |

(Continued)

FOREIGN PATENT DOCUMENTS

| | | |
|---|---|---|
| DE | 256605 A3 | 5/1988 |
| EP | 0232877 B1 | 10/1991 |

(Continued)

OTHER PUBLICATIONS

WO0228405A2 translation. Published Apr. 2002.*
Albertini et al., "Evaluation of Spray Congealing as Technique for the Preparation of Highly Loaded Solid Lipid Microparticles Containing the Sunscreen Agent, Avobenzone," Journal of Pharmaceutical Sciences, 2009, pp. 2759-2769, vol. 98, No. 8.
Bilati et al., "Strategic approaches for overcoming peptide and protein instability within biodegradable nano- and microparticles," Eur J Pharm Biopharm, 2005, pp. 375-88, vol. 59, No. 3.

(Continued)

Primary Examiner — Audrea Buckley
(74) Attorney, Agent, or Firm — The Webb Law Firm (57) ABSTRACT A veterinary pharmaceutical composition, including at least one active veterinary pharmaceutical substance which is selected among gonadorelin and gonadorelin analogs as well as salts of gonadorelin and of the gonadorelin analogs, is provided. The composition includes a liposome-free matrix which delays the release of the active veterinary pharmaceutical substance from the composition, which matrix includes a basic material which is selected from the group consisting of natural and synthetic triglycerides, vegetable oils, diacylpropanediols, diacylbutanediols and mixtures of these substances, the veterinary pharmaceutical composition including no biodegradable polymer.

17 Claims, 6 Drawing Sheets

(56) References Cited

U.S. PATENT DOCUMENTS

| | | | |
|---|---|---|---|
| 8,980,248 B2 | 3/2015 | Shoichet et al. | |
| 2002/0039996 A1* | 4/2002 | Bauer | A61K 9/0019 514/10.6 |
| 2004/0022815 A1 | 2/2004 | Jindal et al. | |
| 2004/0235748 A1 | 11/2004 | Igari et al. | |
| 2004/0241229 A1 | 12/2004 | Yamamoto et al. | |
| 2005/0032762 A1 | 2/2005 | Hubler et al. | |
| 2005/0064039 A1 | 3/2005 | Futo et al. | |
| 2006/0100154 A1 | 5/2006 | Koch et al. | |
| 2006/0216242 A1 | 9/2006 | Rohloff et al. | |
| 2006/0286161 A1 | 12/2006 | Panzner et al. | |
| 2007/0196416 A1 | 8/2007 | Li et al. | |
| 2008/0044450 A1 | 2/2008 | Brandon et al. | |
| 2008/0085263 A1 | 4/2008 | Thuresson et al. | |
| 2008/0118545 A1 | 5/2008 | Futo et al. | |
| 2008/0152675 A1 | 6/2008 | Pouliquen | |
| 2008/0254086 A1 | 10/2008 | Brown et al. | |
| 2009/0004272 A1 | 1/2009 | Gibson et al. | |
| 2009/0317478 A1 | 12/2009 | Han et al. | |
| 2010/0239654 A1 | 9/2010 | Winter | |
| 2011/0091420 A1 | 4/2011 | Liu et al. | |
| 2011/0226188 A1 | 9/2011 | Chen | |
| 2012/0046220 A1 | 2/2012 | Chen et al. | |
| 2013/0251674 A1 | 9/2013 | Fereira et al. | |
| 2015/0017177 A1 | 1/2015 | Houston et al. | |

FOREIGN PATENT DOCUMENTS

| | | | |
|---|---|---|---|
| EP | 0579347 B1 | 4/1996 | |
| EP | 0486959 B1 | 8/1996 | |
| EP | 0668073 B1 | 4/1999 | |
| EP | 0709085 B1 | 1/2001 | |
| EP | 1088555 A1 | 4/2001 | |
| EP | 1457208 A1 | 9/2004 | |
| EP | 1466596 A1 | 10/2004 | |
| EP | 1142567 B1 | 10/2005 | |
| EP | 1017411 B1 | 11/2005 | |
| EP | 1310517 B1 | 4/2006 | |
| EP | 1007080 B1 | 4/2007 | |
| EP | 1768650 B1 | 7/2008 | |
| EP | 1610765 B1 | 8/2008 | |
| EP | 1399133 B1 | 4/2009 | |
| EP | 2210589 A1 | 7/2010 | |
| WO | 9832423 A1 | 7/1998 | |
| WO | 0128555 A1 | 4/2001 | |
| WO | WO01/28555 A1 * | 4/2001 | A61K 31/355 |
| WO | 0187265 A2 | 11/2001 | |
| WO | WO01/87265 A2 * | 11/2001 | A61K 9/08 |
| WO | 0228405 A2 | 4/2002 | |
| WO | 0232395 A2 | 4/2002 | |
| WO | WO02/28405 A2 * | 4/2002 | A61K 38/00 |
| WO | 02087616 A1 | 11/2002 | |
| WO | 2004030687 A1 | 4/2004 | |
| WO | 2004045646 A1 | 6/2004 | |
| WO | 2004100928 A1 | 11/2004 | |
| WO | 2005067889 A1 | 7/2005 | |
| WO | 2005117934 A1 | 12/2005 | |
| WO | 2006004167 A1 | 1/2006 | |
| WO | 2006071208 A1 | 7/2006 | |
| WO | 2006083799 A2 | 8/2006 | |
| WO | 2007084460 A2 | 7/2007 | |
| WO | 2008074871 A1 | 6/2008 | |
| WO | 2008075762 A1 | 6/2008 | |
| WO | 2008113992 A2 | 9/2008 | |
| WO | 2011072399 A1 | 6/2011 | |

OTHER PUBLICATIONS

Bundesamt für Verbraucherschutz und Lebensmittelsicherheit, "Mutual recognition procedured/decentralised procedure: Publicly available assessment report for a veterinary medicinal product," Maprelin 75 µg/ml solution for injection for pigs, 2009, 16 pages.
Bunjes et al., "Influence of emulsifiers on the crystallization of solid lipid nanoparticles," Journal of Pharmaceutical Sciences, 2003, pp. 1509-1520, vol. 92, No. 7.
Christopherson et al., "Solid lipid particles for oral delivery of peptide and protein drugs I—elucidating the release mechanism of lysozyme during lipolysis," Eur J Pharm Biopharm, 2013, pp. 473-480, vol. 85.
European Medicines Agency (EMEA), "Committee for Veterinary Medicinal Products: D-Phe6-Luteinizing-Hormone-Releasing-Hormone: Summary Report," Final, 1996, 2 pages.
European Medicines Agency (EMEA), "Committee for Medicinal Products for Veterinary Use: Perforelin: Summary Report," Final, 2006, 3 pages.
European Medicines Agency, "European public MRL assessment report (EPMAR): Altrenogest (equidae and porcine species)," 2012, pp. 1-15.
Intervet, Inc., "Finding of no significant impact for MATRIX™ (Altrenogest) solution 0.22% for Cycling Gilts," 2003, 9 pages.
Jaspart et al., "Solid lipid microparticles: formulation, preparation, characterisation, drug release and applications," Expert Opin Drug Deliv, 2005, pp. 75-87, vol. 2, No. 1.
Koennings et al. "Influence of wettability and surface activity on release behavior of hydrophilic substances from lipid matrices," J Control Release, 2007, pp. 173-181, vol. 119, No. 2.
Krome, "Environmental impact assessment for veterinary medicinal products: Gonavet Veyx®," Veyx-Pharma-GmbH), 2012, 11 pages.
Landesumweltamt Brandenburg, "Endokrin wirksame Stoffe in der Umwelt: Literaturstudie zur Bedeutung dieser Stoffe im Land Brandenburg," Studien und Tagungsberichte Band 26, 2000 (English-language Abstract).
Larsen et al., "Critical factors influencing the in vivo performance of long-acting lipophilic solutions—impact on in vitro release method design," Aaps J, 2009, pp. 762-770, vol. 11, No. 4.
Larsen et al., "Determination of the disappearance rate of iodine-125 labelled oils from the injection site after intramuscular and subcutaneous administration to pigs," Int J Pharm, 2001, pp. 67-75, vol. 230.
Lorenz et al., "The synthetic gestagen Levonorgestrel impairs metarmorphosis in Xenopus laevis by disruption of the thyroid system," Toxicol. Sci., 2011, pp. 94-102, vol. 123, No. 1.
McCarron et al., "Comparison of a novel spray congealing procedure with emulsion-based methods for the micro-encapsulation of water-soluble drugs in low melting point triglycerides," J Microencapsul, 2008, pp. 365-378, vol. 25, No. 6.
Medlicott et al., "Sustained release veterinary parenteral products," Adv Drug Deliv Rev, 2004, pp. 1345-1365, vol. 56.
Narang et al., "Stable drug encapsulation in micelles and microemulsions," Int J Pharm, 2007, pp. 9-25, vol. 345.
Nippe et al., "Parenteral oil-based drospirenone microcrystal suspensions-evaluation of physicochemical stability and influence of stabilising agents," Int J Pharm, 2011, pp. 181-188, vol. 416.
Rathbone et al., "Long acting animal health drug products: fundamentals and applications," Springer, 2013 (English-language Abstract only).
Reithmeier et al., "Lipid microparticles as a parenteral controlled release device for peptides," J Control Release, 2001, pp. 339-350, vol. 73.
Reithmeier et al., "Development and characterization of lipid microparticles as a drug carrier for somatostatin," Int J Pharm, 2001, pp. 133-143, vol. 218.
Scalia et al., "Comparison of spray congealing and melt emulsification methods for the incorporation of the water-soluble salbutamol sulphate in lipid microparticles," Pharm Dev Technol, 2013, pp. 266-273, vol. 18, No. 1.
Tanaka et al., "Intramuscular absorption of drugs from oily solutions in the rat," Chem Pharm Bull (Tokyo), 1974, pp. 1275-1284, vol. 22.
Vogelhuber et al., "Monolithic triglyceride matrices: a controlled-release system for proteins," Pharm Dev Technol, 2003, pp. 71-79, vol. 8, No. 1.
Wright et al., "Long acting injections and implants," Springer, 2012. (English-language Abstract only).
Yu et al., "Preparation, characterization, and in vivo evaluation of an oil suspension of a bovine growth hormone releasing factor analog," Pharm Sci, 1996, pp. 396-401, vol. 85, No. 4.
Zaky et al., "The mechanism of protein release from triglyceride microspheres," J Control Release, 2010, pp. 202-210, vol. 147.

(56) References Cited

OTHER PUBLICATIONS

Zeilinger, "Aquatische Ökotoxikologie von Arzneimitteh—Die Reproduktionstoxische Wirkung von synthetischen Gestagenen am Fisch (Pimephales promelas)," Dissertation, Kiel, 2009 (English-language Abstract).

Zeilinger et al., "Effects of synthetic gestagens on fish reproduction," Environ. Toxicol. Chem., 2009, pp. 2663-2670, vol. 28, No. 12.

\* cited by examiner

VETERINARY PHARMACEUTICAL COMPOSITION AND USE THEREOF

CROSS-REFERENCE TO RELATED APPLICATIONS

This application is the United States national phase of International Application No. PCT/EP2015/058265 filed Apr. 16, 2015, and claims priority to German Patent Application No. 10 2014 207 353.7 filed Apr. 16, 2014, the disclosures of which are hereby incorporated in their entirety by reference.

BACKGROUND OF THE INVENTION

Field of the Invention

The present invention relates to a pharmaceutical composition and to a method for using the composition.

Description of Related Art

In order to synchronize the sexual cycles in gilts, the hormone Altrenogest has been employed for a long time in order to induce cycle blockade.

Such a cycle synchronization in fertile gilts (sexually mature sows before the first litter) has the aim of synchronizing the estrous and/or ovulation so that artificial insemination may take place while dispensing with a laborious estrous check at defined points in time. Such a cycle synchronization results in decisive advantages for the animals and keepers, which are, inter alia, no searching for animals in estrous over several days, simplification of ordering sperm, sows' simultaneous entry into the pregnancy phase, and concentration of the animal keepers' labor to days and hours capable of being planned.

The activity of the Altrenogest preparations available on the market is reliable. However, the preparations must be considered to be harmful in ecotoxicological terms.

In the case of Levonorgestrel, a hormone whose structure is very similar to Altrenogest, it has already been possible in the past to detect an adverse effect on organisms even at very low concentrations.

Various compositions which allow delayed release of an active substance have already been known from the prior art. However, the structure of these compositions is frequently highly complex and adapted to suit specific active substances.

Thus, WO 2004/100928 A1 describes a liposome-forming slow-release system which is composed of specific lipids.

WO 2005/067889 A1 describes a polymer product which comprises a biodegradable polymer system which ensures a delayed release of active substance.

WO 2005/117934 A1 describes a device for the delayed release of an active substance, with mainly mannitol and dextran being employed as release-delaying substances.

WO 2007/084460 A2 describes an injectable polymeric composition, where a delayed release of active substance is achieved via a biodegradable polymer.

U.S. Pat. No. 4,767,628 A describes pharmaceutical compositions which comprise polylactic acid by way of biodegradable polymer which is employed for the delayed release of an active substance.

U.S. Pat. No. 5,766,627 A describes a multistep process for the preparation of multivesicular liposomes which comprise a plurality of nonconcentric chambers with internal membranes. These liposomes, with their very specific structure, may be employed for the encapsulation and release, at a later point in time, of a biologically active substance.

Accordingly, there are known from the prior art systems and compositions where a delayed release of a pharmaceutical substance is achieved or controlled by liposomes with a specific structure or by means of a biodegradable polymer. As a rule, making such liposomes is very laborious. Moreover, the use of biodegradable polymers is relatively costly. In addition, it entails a relatively high weight and volume of a pharmaceutical composition for a specific amount of active substance since the polymers' intrinsic weight and volume is considerable.

SUMMARY OF THE INVENTION

The present invention is based on the problem of providing a preparation for cycle blockade which is active over a defined period of time, can be prepared and used in a simple manner and is more environmentally friendly than preparations known from the prior art.

This problem is solved with a veterinary pharmaceutical composition with the features as described herein. Such a composition comprises at least one active veterinary pharmaceutical substance, which is gonadorelin and/or one gonadorelin analog or a plurality of gonadorelin analogs and/or one or more salts of gonadorelin and/or of the gonadorelin analog or of the gonadorelin analogs. Gonadorelin is also known by the name Gonadotropin Releasing Hormone 1 (GnRH1). It is a decapeptide with the following structure:

(SEQ ID No. 1)
pyroGlu-His-Trp-Ser-Tyr-Gly-Leu-Arg-Pro-Gly

Gonadorelin analogs are considered to be all those substances which are similar to gonadorelin in terms of structure and/or activity. In particular, they are decapeptides where up to five amino acids, in particular up to four amino acids, in particular up to three amino acids, in particular up to two amino acids and very especially one amino acid is/are exchanged in comparison with gonadorelin's primary structure. In a further variant, precisely five amino acids, precisely four amino acids, precisely three amino acids, precisely two amino acids or precisely one amino acid is/are exchanged in the gonadorelin analogs in comparison with gonadorelin's primary structure.

Suitable salts of gonadorelin or of the gonadorelin analogs are, in particular, water-soluble salts.

Once gonadorelin has been released, it is metabolized very rapidly in the body of an animal. Here, gonadorelin is hydrolyzed to give oligopeptides with a maximum of five amino acids, mainly in the blood plasma, but also in various organs or tissues of the animal. These oligopeptides already are no longer biologically active, so that no toxic or physiologically active metabolites are excreted. As a consequence, gonadorelin and gonadorelin analogs have no negative impact on the environment when employed as active veterinary pharmaceutical substances.

The claimed veterinary pharmaceutical composition is distinguished in that it includes a liposome-free matrix which delays the release of the active veterinary pharmaceutical substance from the composition, which matrix includes a basic material selected from the group consisting of natural and synthetic triglycerides, vegetable oils (refined or unrefined), diacylpropanediols, diacylbutanediols and mixtures of these substances, the veterinary pharmaceutical composition comprising no biodegradable polymer. Examples of biodegradable polymers are those which are described in WO 2005/067889 A1, WO 2007/084460 A2 and/or U.S. Pat. No. 4,767,628 A.

The term "liposome-free" should be construed such in this context that a maximum of 5%, in particular a maximum of 4%, in particular a maximum of 3%, in particular a maximum of 2%, in particular a maximum of 1%, in particular a maximum of 0.5%, in particular a maximum of 0.01% and very especially no molecules at all of the basic material in the composition form liposomes. The liposome-free configuration of the claimed veterinary pharmaceutical composition allows the simple preparation of this composition. Thus, it is not necessary to mix certain aqueous and non-aqueous phases with each other, following specific protocols, in order to achieve good liposome formation. Rather, such liposomes are not required in the first place by way of structures in order to ensure, with the presently claimed basic materials for the matrix, a delayed release of the active veterinary pharmaceutical substance. If the present veterinary pharmaceutical composition comprises a very low liposome content, such liposomes have formed spontaneously and do not have the purpose of influencing the composition's release of active substance. Rather, the latter is achieved by the selection of the basic materials per se and not by their arrangement to give specific microspheric structures such as, for example, liposomes.

In one variant, the veterinary pharmaceutical component does not contain any acid, in particular no perchloric acid, no nitric acid, no formic acid, no sulfuric acid, no phosphoric acid, no acetic acid, no glucuronic acid, no citric acid, no trichloroacetic acid, no trifluoroacetic acid and/or no salts of these acids.

The release of the veterinary pharmaceutical substance from the composition is preferably effected at a veterinary pharmaceutically active dosage. In this context, a dosage considered to be veterinary pharmaceutically active is one that suffices to suppress estrous in the animals treated with this dosage. Examples of veterinary pharmaceutically active dosages are specified further below. A veterinary pharmaceutically active dosage is higher than a veterinary pharmaceutically inactive dosage. A veterinary pharmaceutically inactive dosage is, in particular, a dosage of less than 10 micrograms per 24 hours, in particular not more than 9 micrograms per 24 hours, in particular not more than 8 micrograms per 24 hours, in particular not more than 7 micrograms per 24 hours, in particular not more than 6 micrograms per 24 hours, in particular not more than 5 micrograms per 24 hours, in particular not more than 4 micrograms per 24 hours, in particular not more than 3 micrograms per 24 hours, in particular not more than 2 micrograms per 24 hours, in particular not more than 1 microgram per 24 hours and is very especially less than 1 microgram per 24 hours. In other words, the veterinary pharmaceutical composition is an active veterinary pharmaceutical substance as slow-release formulation. This slow-release formulation ensures that the active substance (that is to say the active veterinary pharmaceutical substance) is released from the composition in a veterinary pharmaceutically active dosage over the desired period of time.

By virtue of the prolonged activity of the veterinary pharmaceutical composition, only a single application is required in order to achieve the desired effect of the composition over the release period. This simplifies handling the composition and the treatment of the animals.

In one variant, the active substance is released at a veterinary pharmaceutically active dosage only over a period of up to 25 days, in particular up to 24 days, in particular up to 23 days, in particular up to 22 days, in particular up to 21 days, in particular up to 20 days, in particular up to 19 days, in particular up to 18 days, in particular up to 17 days, in particular up to 16 days, in particular up to 15 days, in particular up to 14 days, in particular up to 13 days, in particular up to 12 days and very especially up to 10 days after the application of the veterinary pharmaceutical composition. In this manner, a particularly advantageous way of synchronizing the cycle of the treated animals may be achieved, depending on the animal to be treated. In a further variant, the active substance is released at a veterinary pharmaceutically active dosage over a period of precisely 25 days, in particular only during a period of precisely 24 days, in particular precisely 23 days, in particular precisely 22 days, in particular precisely 21 days, in particular precisely 20 days, in particular precisely 19 days, in particular precisely 18 days, in particular precisely 17 days, in particular precisely 16 days, in particular precisely 15 days, in particular precisely 14 days, in particular precisely 13 days, in particular precisely 12 days and very especially precisely 10 days after the application of the veterinary pharmaceutical composition.

In a further variant, the active substance is released at a veterinary pharmaceutically active dosage during a period of from 10 to 25 days, in particular 11 to 24 days, in particular 12 to 23 days, in particular 13 to 22 days, in particular 14 to 21 days, in particular 15 to 20 days, in particular 16 to 19 days, in particular 17 to 18 days, in particular 14 to 18 days, in particular 15 to 18 days and very especially of from 16 to 17 days after the application of the veterinary pharmaceutical composition.

In a further variant, the veterinary pharmaceutical composition is provided as such a slow-release formulation in which the release of the active substance at the end of the release period chosen ends essentially abruptly. That is to say, the active substance concentration in the treated organism will, as the result of a defined and sudden drop in the release dosage of the active substance, diminish within a very short period of time to below a veterinary pharmaceutically active concentration. Because gonadorelin had previously been released at a veterinary pharmaceutically active dosage over a prolonged period of time, the gonadorelin receptor will be down regulated and the pituitary gland (and other compartments of the treated organism) will be desensitized to gonadorelin. As a result, the luteinizing hormone and the follicle-stimulating hormone, which are essential to follicle development, are not secreted. As a consequence, follicle development on the ovary is inhibited so that estrous of the treated organism does not take place. After reversing the blockade of the gonadorelin receptor by ending the release of active substance, follicle growth resumes so that a new sexual cycle may begin.

In one variant, gonadorelin[6-D-Phe] is employed as active substance. This gonadorelin analog differs from gonadorelin only in that it comprises, at position 6, a D-phenylalanine instead of the glycine in gonadorelin. The primary structure of this gonadorelin analog is therefore as follows:

(SEQ ID No. 2)
pyroGlu-His-Trp-Ser-Tyr-D-Phe-Leu-Arg-Pro-GlyNH$_2$

Gonadorelin[6-D-Phe] has proven to be a particularly well tolerated and effective active substance for controlling the cycle in female animals. In particular, all of the abovementioned properties of gonadorelin also apply to gonadorelin[6-D-Phe]. Preferably, gonadorelin[6-D-Phe] is employed as the only active veterinary pharmaceutical substance.

In one variant, the matrix includes an emulsifier. By adding such an emulsifier, it can be ensured in a particularly simple and safe manner that the triglycerides, vegetable oils, diacylpropanediols and/or diacylbutanediols which are present in the matrix do not form any liposomes. Therefore, a veterinary pharmaceutical composition which includes a matrix as defined hereinabove and an emulsifier can be considered to be a liposome-free veterinary pharmaceutical composition even without the explicit expression "liposome-free" since this is already implicit due to the presence of an emulsifier.

The present invention therefore also relates to a veterinary pharmaceutical composition, comprising at least one active veterinary pharmaceutical substance which is selected among gonadorelin and gonadorelin analogs and salts of gonadorelin and gonadorelin analogs, wherein the composition includes a matrix which delays the release of the active veterinary pharmaceutical substance from the composition and an emulsifier, wherein the matrix includes a basic material selected from the group consisting of natural and synthetic triglycerides, vegetable oils, diacylpropanediols, diacylbutanediols and mixtures of these substances, the veterinary pharmaceutical composition comprising no biodegradable polymer.

In one variant, the emulsifier is a monoglyceride, diglyceride, partial glyceride, sorbitan fatty acid ester, fatty alcohol, lecithin, cholesterol and/or an ester of polyethylene glycol (PEG) and an oil.

In a further variant, the emulsifier is glycerol monostearate, glycerol monopalmitate, glycerol distearate, glycerol dimyristate, glycerol dipalmitate, glycerol monocaprylate, glycerol stearate citrate, glycerol stearate, glycerol monocaprylocaprate type I, glycerol cocoate, glycerol monooleate, sorbitan trioleate, sorbitan monolaurate, sorbitan monopalmitate, sorbitan monostearate, sorbitan tristearate, sorbitan monooleate, sorbitan sesquioleate, cetylstearyl alcohol, cetyl alcohol, stearyl alcohol, myristyl alcohol, behenyl alcohol, lecithin, cholesterol, phosphatidylcholine, esterified phosphatidylcholine, (1,2-dimyristoyl-sn-glycero-3-phosphocholine), (1-palmitoyl-2-oleoyl-sn-glycero-3-phosphocholine), sorbitan monolaurate, sorbitan monopalmitate, sorbitan monostearate, sorbitan tristearate, sorbitan monooleate, sorbitan sesquioleate, sorbitan trioleate, polyoxyethylene(20) sorbitan monolaurate, polyoxyethylene(20) sorbitan monopalmitate, polyoxyethylene(20) sorbitan monostearate, polyoxyethylene(20) sorbitan tristearate, polyoxyethylene(20) sorbitan monooleate, polyoxyethylene(20) sorbitan trioleate, macrogol glycerol ricinoleate (35), macrogol glycerol ricinoleate (40), PEG-6-almond kernel oil, PEG-6-almond oil, PEG-6-groundnut oil, PEG-6-olive oil, PEG-6-corn oil, PEG-6-palm kernel oil, PEG-6-hydrogenated palm kernel oil and/or PEG-8-corn oil.

Examples of emulsifiers which may be employed are the following:

| Trade name | Composition | Name |
|---|---|---|
| Ionic emulsifiers | | |
| Phospholipon ®90H | 90% hydrogenated soybean phosphatidylcholine | |
| Phospholipon ®90G | 90% hydrogenated soybean phosphatidylcholine (granules) | |
| Phospholipon ®100H | 98% fully hydrogenated soybean phosphatidylcholine | |
| LIPOID S PC-3 | 98% fully hydrogenated soybean phosphatidylcholine (parental administration) | |
| LIPOID PC 14:0/14:0 | Pure phosphatidylcholine esterified with myristic acid at position 1 and at position 2 (OH group 1, OH group 2) | DMPC (1,2-dimyristoyl-sn-glycero-3-phosphocholine) |
| LIPOID PC 16:0/18:1 | Pure phosphatidylcholine esterified with palmitic acid at position 1 and oleic acid at position 2 (OH group 1, OH group 2) | POPC (1-palmitoyl-2-oleoyl-sn-glycero-3-phosphocholine) |
| Nonionic Emulsifiers | | |
| Span ® 20 | | Sorbitan monolaurate |
| Span ® 40 | | Sorbitan monopalmitate |
| Span ® 60 | | Sorbitan monostearate |
| Span ® 65 | | Sorbitan tristearate |
| Span ® 80 | | Sorbitan monooleate |
| Span ® 83 | | Sorbitan sesquioleate |
| Span ® 85 | | Sorbitan trioleate |
| Tween ® 20 | | Polyoxyethylene(20) sorbitan monolaurate |
| Tween ® 40 | | Polyoxyethylene(20) sorbitan monopalmitate |
| Tween ® 60 | | Polyoxyethylene(20) sorbitan monostearate |
| Tween ® 65 | | Polyoxyethylene(20) sorbitan tristearate |
| Tween ® 80 | | Polyoxyethylene(20) sorbitan monooleate |
| Tween ® 85 | | Polyoxyethylene(20) sorbitan trioleate |
| Kolliphor ™ ELP | Macrogol glycerol ricinoleate - hydrogenated castor oil (composed of 98% ricinoleic acid) ethoxylated at the OH group with different amounts of ethylene oxide (5-200) | Macrogol glycerol ricinoleate (35) parenteral administration |
| Kolliphor ™ EL | — | Macrogol glycerol ricinoleate (35) |
| Kolliphor ™ RH 40 | — | Macrogol glycerol ricinoleate (40) |
| Labrafil ® M1944CS | Transesterification of apricot kernel oil with PEG | PEG-6-apricot kernel oil |
| Labrafil ® M 1966CS | Transesterification of almond oil with PEG | PEG-6-almond oil |
| Labrafil ® M 1969CS | Transesterification of groundnut oil with PEG | PEG-6-groundnut oil |
| Labrafil ® M 1980CS | Transesterification of olive oil with PEG | PEG-6-olive oil |

| Trade name | Composition | Name |
|---|---|---|
| Labrafil ® M 2125CS | Transesterification of corn oil with PEG | PEG-6-corn oil |
| Labrafil ® M 2130CS | Transesterification of palm kernel oil with PEG | PEG-6-palm kernel oil |
| Labrafil ® M 2130BS | Transesterification of hydrogenated palm kernel oil with PEG | PEG-6-hydrogenated palm kernel oil |
| Labrafil ® WL2609BS | Transesterification of corn oil with PEG | PEG-8-corn oil |

In one variant, the veterinary pharmaceutical composition is a one-phase solution or a dispersion of the veterinary pharmaceutical substance (that is to say of the active substance) in a dispersion medium, the dispersion medium being a single phase. In particular, this takes the form of an oily phase, in each case. Such a one-phase configuration can, in an effective manner, avoid liposome formation. Therefore, in this variant, the word "liposome-free" may again be dispensed with when describing the relevant veterinary pharmaceutical composition (compare, in this context, the wording hereinabove). This is because freedom from liposomes results implicitly from the one-phase configuration of the composition. In this context, the dispersion can be, for example, a suspension. The dispersion is preferably precisely not an emulsion. The dispersion medium may also be solid, so that the veterinary pharmaceutical composition may be configured as a porous solid body (porous foam) or as a solid mixture.

In a further variant, the basic material is selected from the group consisting of glycerol tripalmitate, glycerol tristearate, glycerol trimyristate, glycerol tribehenate, glycerol tricaprylate, glycerol tri(caprylate/caprate), glycerol tri(caprylate/caprate/linolate), glycerol tri(caprylate/caprate/laurate) and glycerol tri(caprylate/caprate/succinate), and mixtures of these substances.

The following triglycerides, diacylpropanediols and diacylbutanediols are examples of suitable basic materials:

| Trade name | Composition | Caprylic acid [%] | Capric acid [%] |
|---|---|---|---|
| Miglyol ® 808 | Triglyceride of caprylic acid | 100 | |
| Miglyol ® 810 | Triglyceride of caprylic acid/capric acid | 65-75 | 25-35 |
| Miglyol ® 812 | Triglyceride of caprylic acid/capric acid | 50-65 | 30-45 |
| Miglyol ® 818 | Triglyceride of caprylic acid/capric acid/linolic acid | 45-60 | 25-40 |
| Miglyol ® 8108 | Triglyceride of caprylic acid/capric acid | * | * |
| Miglyol ® 829 | Triglyceride of caprylic acid/capric acid/succinic acid | * | * |
| Miglyol ® 840 | Propylene glycol dicaprylate dicaprate | 65-80 | 15-30 |
| Miglyol ® 8810 | Butylene glycol dicaprylate dicaprate | * | * |
| Neobee ® 0 | Triglyceride of caprylic acid/capric acid | * | * |
| Neobee ® M5 | Triglyceride of caprylic acid/capric acid | * | * |
| Neobee ® M-20 | Propylene glycol dicaprylate dicaprate | * | * |
| Captex ® 355 | Triglyceride of caprylic acid/capric acid | 55 | 42 |
| Captex ® 350 | Triglyceride of caprylic acid/capric acid/lauric acid | * | * |
| Captex ®810D | Triglyceride of caprylic acid/capric acid/linolic acid | * | * |
| Captex ®200P | Propylene glycol dicaprylate dicaprate | * | * |
| Labrafac ™ lipophile WL 1349 | Triglyceride of caprylic acid/capric acid | * | * |
| Labrafac ™PG | Propylene glycol dicaprylate dicaprate | * | * |
| Crodamol ™ GTCC | Triglyceride of caprylic acid/capric acid | * | * |
| Estol ® 1526 | Propylene glycol dicaprylate dicaprate | * | * |

*No precise percentages regarding the composition are available for these substances.

In one variant, the basic material is selected from the group consisting of castor oil, groundnut oil, sesame seed oil, wheat germ oil, cotton seed oil, corn oil, palm oil, coconut oil, palm kernel oil, almond oil, olive oil, soyabean oil, rapeseed oil, sunflower oil, linseed oil, poppyseed oil, rapeseed oil, grape seed oil, jojoba oil, oil of evening primrose, mustard seed oil and mixtures of these oils.

In a further variant, the basic material is selected from the group consisting of propylene glycol di(caprylate/caprate) and butylene glycol di(caprylate/caprate) and mixtures of these substances.

In a further variant, the active substance is then plunged in microcapsules or microparticles, in particular by melt dropping, which ensure the delayed release of the active substance from the composition over a defined release period.

In a further variant, the veterinary pharmaceutical composition is present in such a formulation that it achieves a release of the active substance at a dosage of 10 to 1000 micrograms per 24 hours, in particular 20 to 900 micrograms per 24 hours, in particular 25 to 800 micrograms per 24 hours, in particular 30 to 700 micrograms per 24 hours, in particular 40 to 600 micrograms per 24 hours, in particular 50 to 500 micrograms per 24 hours, in particular 60 to 400 micrograms per 24 hours, in particular 70 to 300 micrograms per 24 hours, in particular 80 to 200 micrograms per 24 hours, and very specially 90 to 100 micrograms per 24 hours. Such a release dosage achieves a concentration in the treated organism which is sufficient for the desired effect. In other words, this dosage is a veterinary pharmaceutically active dosage.

In one variant, the veterinary pharmaceutical substance is released shortly (for example a few hours up to 1 day, 2 days, 3 days or 4 days) after the application in a larger dosage than at a later point in time (for example 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days or 25 days after the application). This effect is also referred to as a rapid rise.

In a further variant, the veterinary pharmaceutical composition is provided as a dimensionally stable formulation. Such dimensionally stable formulations such as, for example, microcapsules or microparticles, are particularly suitable as implants from which active substance is then released during the release period. Such implants may likewise be injected by means of a suitable injector, in particular an ordinary syringe. It is the matrix which acts as support material for the active substance that imparts the dimensional stability to dimensionally stable formulations.

In a further variant, the veterinary pharmaceutical composition comprises at least one additive. This additive may be a porosity agent, a lipid, a phospholipid, a thickener and/or a partial glyceride. In this context, porosity agents are understood as meaning those agents which act for generating pores in a different substance. For example, suitable porosity agents may generate pores in a matrix when the veterinary pharmaceutical composition is present as a dimensionally stable formulation. Examples of suitable porosity agents are polyethylene glycol or a sugar such as, for example, glucose, fructose or sucrose. Mixtures of various porosity agents are also feasible.

Substances which are particularly suitable as basic material of the matrix for dimensionally stable formulations are substances with a low melting point, that is to say a melting point of 50° C. or less, in particular 45° C. or less, in particular 40° C. or less, but higher than the body temperature of the organism to be treated. In pigs, the body temperature is 38.8±0.3° C.

In a further variant, the formulation of the veterinary pharmaceutical composition is chosen such that the composition is present as a non-dimensionally stable formulation, for example as a suspension or a gel. Oily suspensions are particularly preferred in this context. By adjusting the viscosity of the formulation and the particle size of the active substance, it is possible to influence the stability of the composition and the release of active substance from the composition.

In a further variant, the veterinary pharmaceutical composition is present as an emulsion. Gels, suspensions and emulsions can readily be administered by means of injection to an organism to be treated. As explained hereinabove, a single application of the veterinary pharmaceutical composition suffices in order to achieve an activity of the active substance over the release period.

Substances which are particularly suitable as the basic material for the matrix of non-dimensionally stable formulations are substances with a melting point which is lower than the body temperature of the organism to be treated, in particular 37° C. or lower and very especially 35° C. or lower, in particular 30° C. or lower, in particular 25° C. or lower and very especially 20° C. or lower.

If substances such as, for example, vegetable oils have no precisely defined melting point, but a melting range, the upper limit of the melting range should be equated to the melting point as per the above definitions.

The viscosity of a non-dimensionally stable formulation of the veterinary pharmaceutical composition can be adjusted using thickeners. Furthermore, the rigidity of the matrix may be influenced in this manner if the veterinary pharmaceutical composition is present as a dimensionally stable formulation.

Phospholipids and partial glycerides are, as a rule, water-dispersible and, in this manner, can likewise influence the viscosity of the suspension or the rigidity of the matrix. As a consequence, all these additives may be employed for influencing the release of active substance from the veterinary pharmaceutical composition. Thus, the active substance can be released markedly more readily from a matrix which has a high porosity and which starts melting even at the body temperature of those animals in which the veterinary pharmaceutical composition is to be employed than from a matrix which has a lower porosity and which is solid even at higher temperatures.

A further factor which is decisive for the release of the active substance and the stability of the veterinary pharmaceutical composition is the particle size of the active substance. Thus, the active substance is, as a rule, ground before being introduced into the veterinary pharmaceutical composition. Depending on the degree of grinding, the result in this manner is differently sized active substance particles which permit different rates of release of the active substance. By matching the concentration and the nature of the auxiliary, of the size and nature of the active substance particles and optionally the nature and amount of the additive, it is possible thus to provide a veterinary pharmaceutical composition with the desired release of active substance.

The lipids envisaged as auxiliaries or additives—as well as the active substance itself—may be introduced into the veterinary pharmaceutical composition in the form of microparticles. In this context, the mode of action of such auxiliaries or additives in the form of microparticles differs from when these substances are present in larger particles.

In particular, it is envisaged to employ a thickener by way of additive if the veterinary pharmaceutical composition is present as a non-dimensionally stable formulation (for example as suspension). Furthermore, it is envisaged in particular to employ a phospholipid by way of additive if the veterinary pharmaceutical composition is present as a non-dimensionally stable formulation.

The use of a porosity agent is envisaged in particular if the veterinary pharmaceutical composition is present as a dimensionally stable formulation. Furthermore, the use of lipid microparticles is likewise envisaged in particular if the formulation of the veterinary pharmaceutical composition is dimensionally stable.

A further variant for influencing the release of active substance from the veterinary pharmaceutical composition is to alter the matrix of a dimensionally stable formulation itself. This can be done for example by altering the concentration of the matrix substance or by different matrix substances. In this variant, it is not necessary to admix further additives to the matrix. In principle, however, the matrix itself may also be altered, and additives may be added.

In one variant, the invention also relates to a veterinary pharmaceutical composition which comprises at least one active veterinary pharmaceutical substance, which is gonadorelin and/or a gonadorelin analog or several gonadorelin analogs and/or one or more salts of gonadorelin and/or of the gonadorelin analog or the gonadorelin analogs, the composition comprising at least one auxiliary which, in a specific manner, delays the release of the active veterinary pharmaceutical substance from the composition. Thus, the auxiliary interacts with the pharmaceutically active substance such that the active veterinary pharmaceutical substance is released, at a veterinary pharmaceutically active dosage, only during a period of up to 18 days after application of the veterinary pharmaceutical composition.

In one variant, the auxiliary is a glyceride such as, for example, a natural triglyceride, a synthetic triglyceride or partial glyceride, a fatty acid, a fatty acid salt, a fatty acid ester, a lecithin, a polyester, a polyanhydride, a polysaccharide, a semi-synthetic polysaccharide derivative, a polyacrylate, a polyethylene glycol, a polypropylene glycol, a polyester and/or an N-methylpyrrolidone. Examples of suitable fatty acid salts are a stearate and/or a palmitate. Examples of suitable fatty acid esters are fatty acid esters with long-chain alcohols (comprising more than 8 carbon atoms) such as, for example, waxes or fatty acid esters with short-chain alcohols (comprising 8 and fewer carbon atoms, in particular 2 or 3 carbon atoms) such as, for example, esters or partial esters with glycerol or propylene glycol.

Examples of suitable polysaccharides are hyaluronic acid or hydroxyethylcellulose. Examples of suitable polyesters are lactic acid polymers or lactic acid copolymers. Instead of individual substances from the abovementioned groups, it is, naturally, also possible to employ a plurality of substances of the individual groups together and also in combination with one or more substances from others of the abovementioned groups. The composition of the auxiliary brings about a delayed release of the active substance from the veterinary pharmaceutical composition, so that their slow-release effect is established in a particularly advantageous manner.

In a further variant, the auxiliary is aluminum stearate and/or dextrin palmitate. These two substances have proven to be particularly advantageous substances for achieving the desired slow-release effect, both individually and in combination. Moreover, they are highly compatible and easy to process.

In a further variant, the auxiliary is polylactic polyglycolic acid. This lactic acid copolymer, too, has proven to be particularly advantageous for achieving the desired slow-release effect.

In one variant, the dimensionally stable formulation includes a glyceride by way of matrix and/or auxiliary. Suitable for this purpose are, in particular, natural or synthetic triglycerides. However, monoglycerides or diglycerides (partial glycerides) have also proven to be suitable matrices and/or auxiliaries for dimensionally stable formulations of the veterinary pharmaceutical composition.

The present invention also relates to the use of a veterinary pharmaceutical composition as per the previous explanations in controlling the cycle of (female) animals. Thus, the veterinary pharmaceutical composition can be used in particular for the cycle blockade and cycle synchronization of (female) animals. The animals are preferably mammals, in particular rodents or cloven-hoofed animals. In this context, the expression "animal" does not include the expression "human".

In one variant there is envisaged a parenteral, in particular intravenous, application of the veterinary pharmaceutical composition.

According to the mechanism of action illustrated hereinabove, an administration of gonadorelin or a gonadorelin analog will inhibit the secretion of the lutenizing hormone and of the follicle-stimulating hormone over a prolonged period. As a consequence, follicle development on the ovary of the treated animal is inhibited. At the end of the release of active substance, follicle growth resumes so that a new sexual cycle may begin. By administering the above-described veterinary pharmaceutical composition it is therefore possible to synchronize the sexual cycle of all female animals of a group such that artificial insemination may take place at a defined point in time without laborious estrous checks. Thus, the veterinary pharmaceutical composition described herein can be employed for cycle synchronization like veterinary pharmaceuticals known from the prior art. However, the veterinary pharmaceutical composition described herein has advantageous environmental properties, as has been illustrated hereinabove. Moreover, it only needs to be administered once so as to achieve cycle synchronization in individual animals of a group.

Preferably, the veterinary pharmaceutical composition is employed for controlling the cycle of gilts. Owing to the relatively high number of pigs which are kept together in one sty and/or in one group, cycle synchronization of gilts benefits from particularly many advantages of the veterinary pharmaceutical composition described. In principle, however, it may also be employed in other animals, such as, for example, mares or bitches. Therefore, the presently described novel veterinary pharmaceutical composition can be employed in the same fields of application as the veterinary pharmaceuticals which are already known from the prior art but which do not have the advantageous environmental properties of the present composition. Furthermore, the presently claimed veterinary pharmaceutical composition only needs to be applied once in order to display its advantageous properties. This considerably reduces the labor involved in their use and the stress for the treated animals which this entails.

All variants of the veterinary pharmaceutical compositions described also apply analogously to the described method for using of these compositions, and vice-versa. All variants may be combined with each other as desired.

BRIEF DESCRIPTION OF THE DRAWINGS

Further details of the veterinary pharmaceutical composition described are illustrated in greater detail below with reference to figures and use examples.

DETAILED DESCRIPTION OF THE INVENTION

Figure 1:
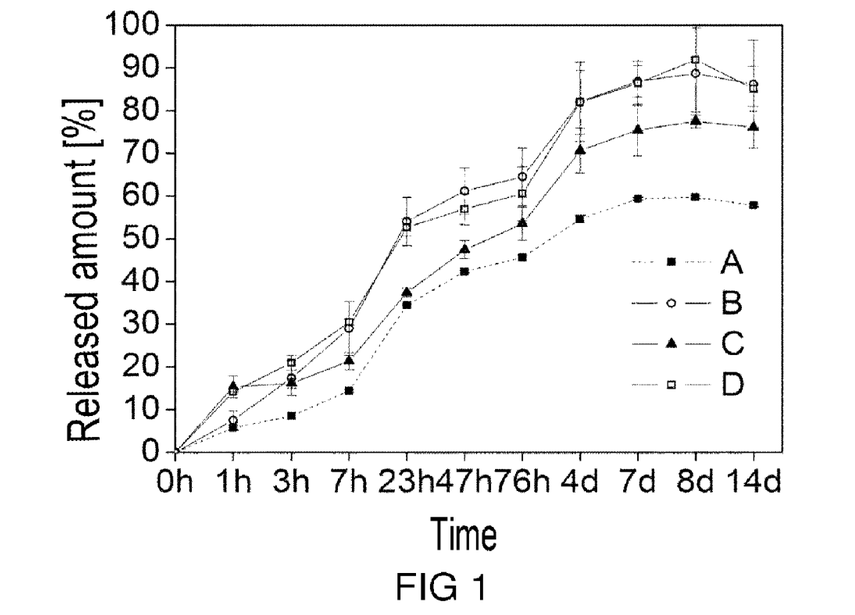
FIG. 1 shows four in-vitro release kinetics of gonadorelin [6-D-Phe]-acetate in various oily suspensions as matrices.

FIG. 1 shows four in-vitro release kinetics of gonadorelin [6-D-Phe]-acetate in various oily suspensions. Here, the release is in each case delayed in comparison with a matrix which does not delay the release.

The following materials besides gonadorelin[6-D-Phe]-acetate were used for the experiments, whose results are shown of FIG. 1:

| Product | Description |
|---|---|
| Castor oil | Refined oil |
| Miglyol ® 812 | Triglyceride of caprylic acid/capric acid |

The following formulations were made in order to determine the release kinetics:

| Formulation | Viscosity [mPas] | Gonadorelin[6-D-Phe]-acetate concentration [µg/ml] | Castor oil, parts by volume | Miglyol ® 812, parts by volume |
|---|---|---|---|---|
| A | 450 | 1875 | 9 | 1 |
| B | 120 | 1875 | 1 | 1 |
| C | 450 | 375 | 9 | 1 |
| D | 120 | 375 | 1 | 1 |

In order to prepare the individual suspensions, the castor oil was mixed with the Miglyol at 60° C. under nitrogen in the ratio 9:1. Thereafter, the mixture was cooled to 25° C., and lyophilized gonadorelin[6-D-Phe]-acetate was added. The mixture was homogenized for five minutes at 2000 rpm using an Ultra-Turrax. Thereafter, the solution was diluted with castor oil and/or Miglyol so as to arrive at the gonadorelin[6-D-Phe]-acetate concentrations and viscosities shown in the above table.

Thereafter, the release was determined over 14 days, with the curves A, B, C and D of FIG. 1 showing the release of the gonadorelin[6-D-Phe]-acetate from the formulations A, B, C and D shown in the above table.

The release kinetics shown in FIGS. 2 to 10 relate to the release of gonadorelin[6-D-Phe] as active substance from dimensionally stable matrices which were obtained as described in the following experimental set-up: 50 mg of particles (comprising matrix and active substance) were placed into a dialysis tube with a cut-off of 12000-14000 Da and dispersed in 2 ml of phosphate-buffered sodium chloride buffer (PBS buffer). Gonadorelin-6-D[Phe] has a molecular weight of approximately 1000 Da and was able to pass readily through the dialysis membrane.

The dialysis tube was sealed and placed into a tube with a further 15 ml of PBS buffer. The subsequent dialysis was carried out at 39° C. At defined points in time, 1 ml of samples were taken from the dialysate, and the volume removed was replaced by fresh buffer. The amount of the gonadorelin[6-D-Phe] released from the particles was determined in the samples taken.

Figure 2:
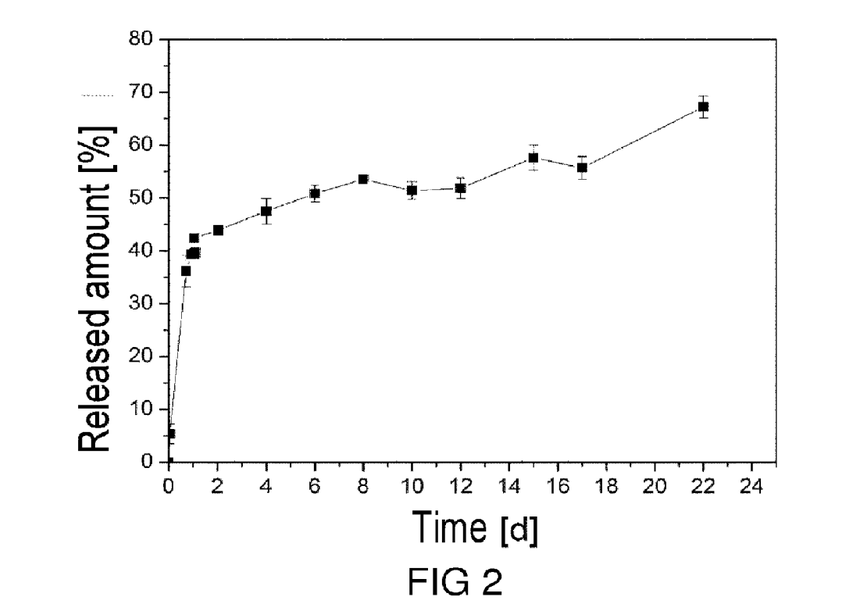
FIG. 2 shows one in-vitro release kinetic of gonadorelin [6-D-Phe] from a matrix composed of glycerol tripalmitate+10% glycerol monostearate (GMS).
Figure 3:
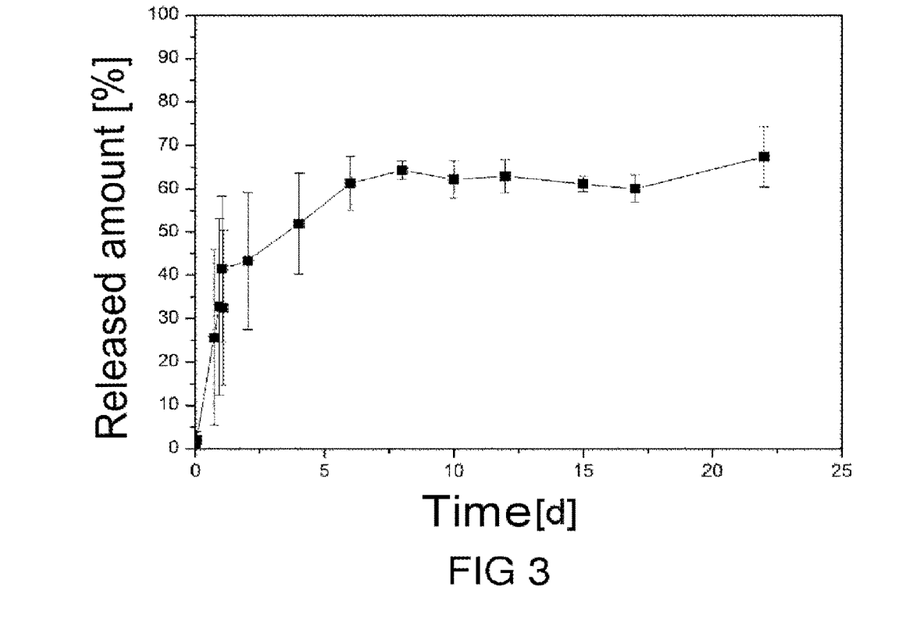
FIG. 3 shows one in-vitro release kinetic of gonadorelin [6-D-Phe] from a matrix composed of glycerol tripalmitate+20% GMS.
Figure 4:
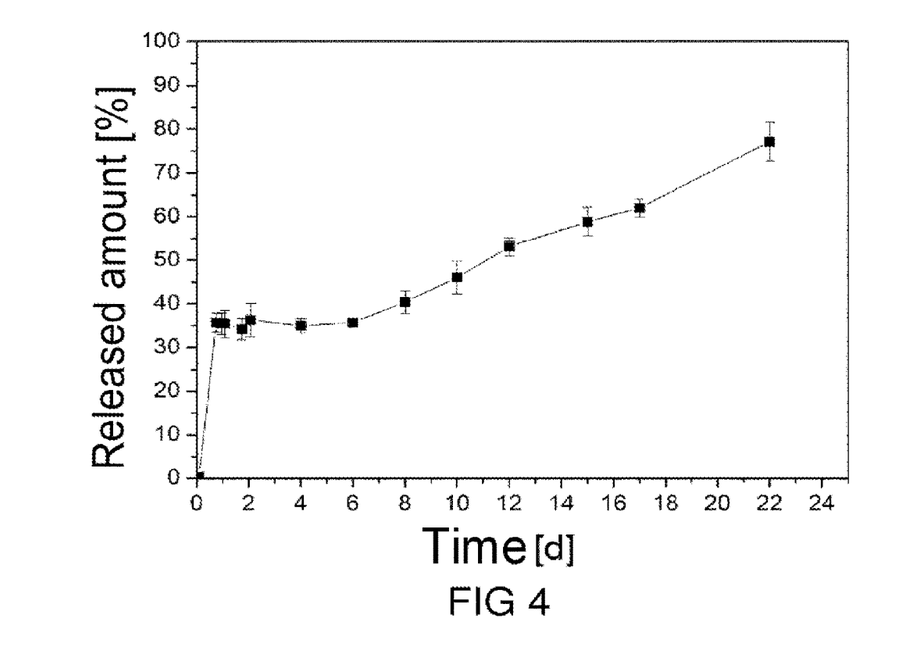
FIG. 4 shows one in-vitro release kinetic of gonadorelin [6-D-Phe] from a matrix composed of glycerol tristearate+10% GMS.
Figure 5:
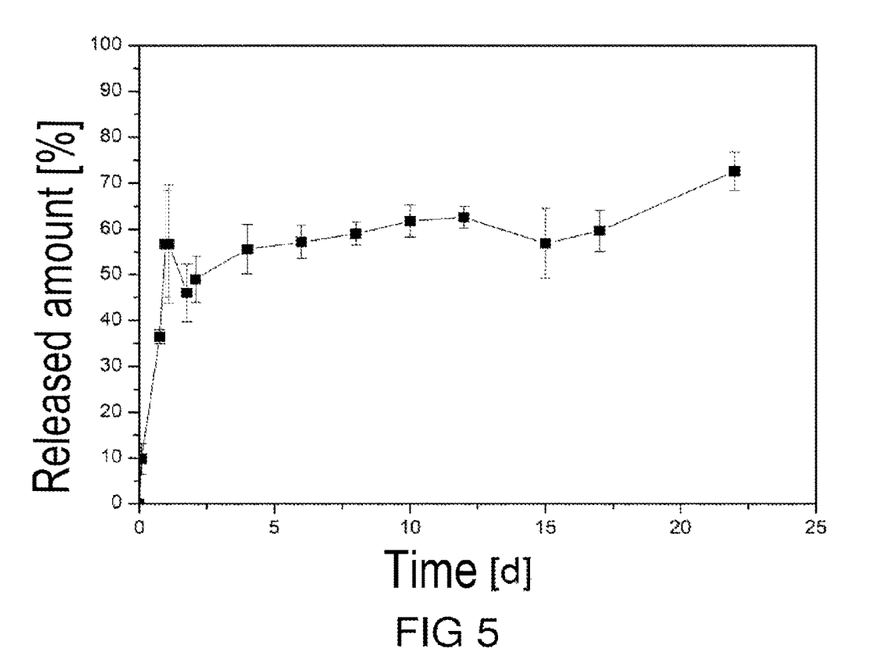
FIG. 5 shows one in-vitro release kinetic of gonadorelin [6-D-Phe] from a matrix composed of glycerol tristearate+20% GMS.
Figure 6:
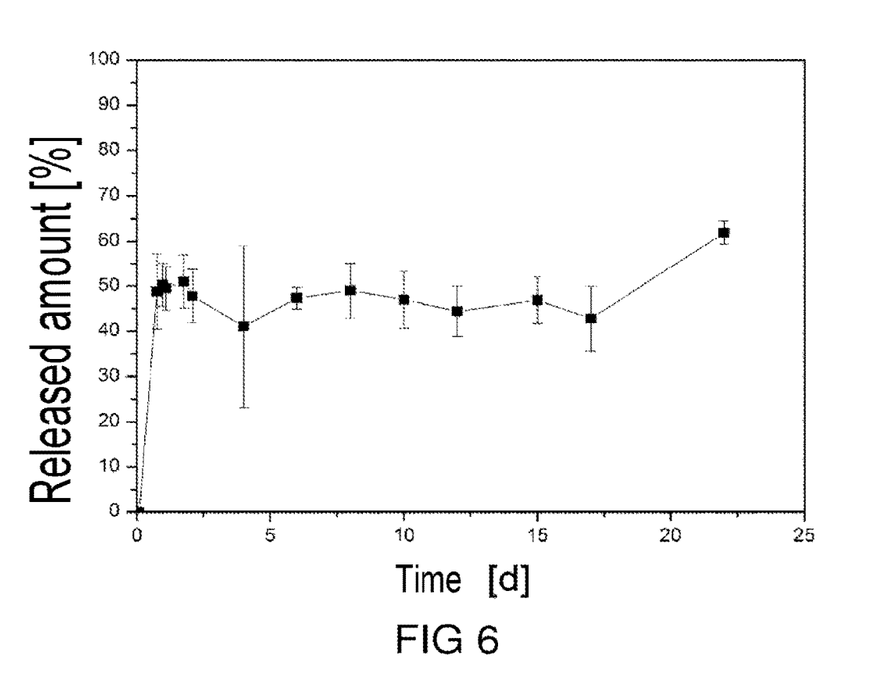
FIG. 6 shows one in-vitro release kinetic of gonadorelin [6-D-Phe] from a matrix composed of glycerol tristearate+40% GMS.
Figure 7:
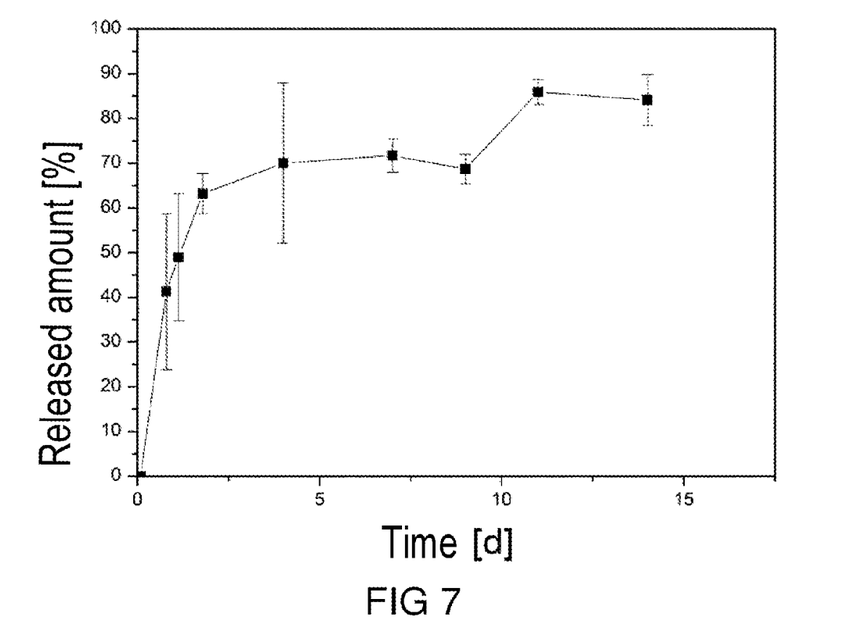
FIG. 7 shows one in-vitro release kinetic of gonadorelin [6-D-Phe] from a matrix composed of glycerol tripalmitate+10% cetyl stearyl alcohol (CSA).
Figure 8:
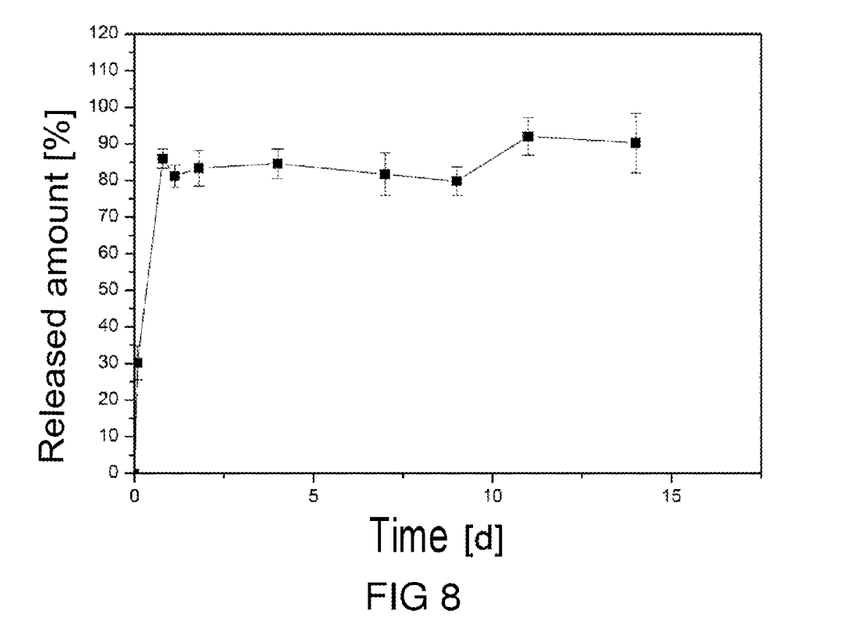
FIG. 8 shows one in-vitro release kinetic of gonadorelin [6-D-Phe] from a matrix composed of glycerol tripalmitate+20% CSA.
Figure 9:
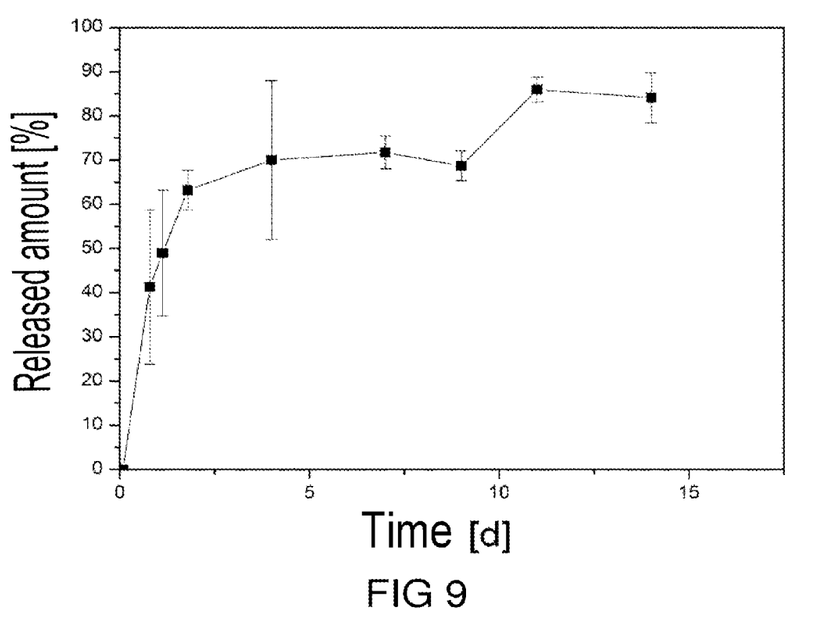
FIG. 9 shows one in-vitro release kinetic of gonadorelin [6-D-Phe] from a matrix composed of glycerol tripalmitate+60% CSA.
Figure 10:
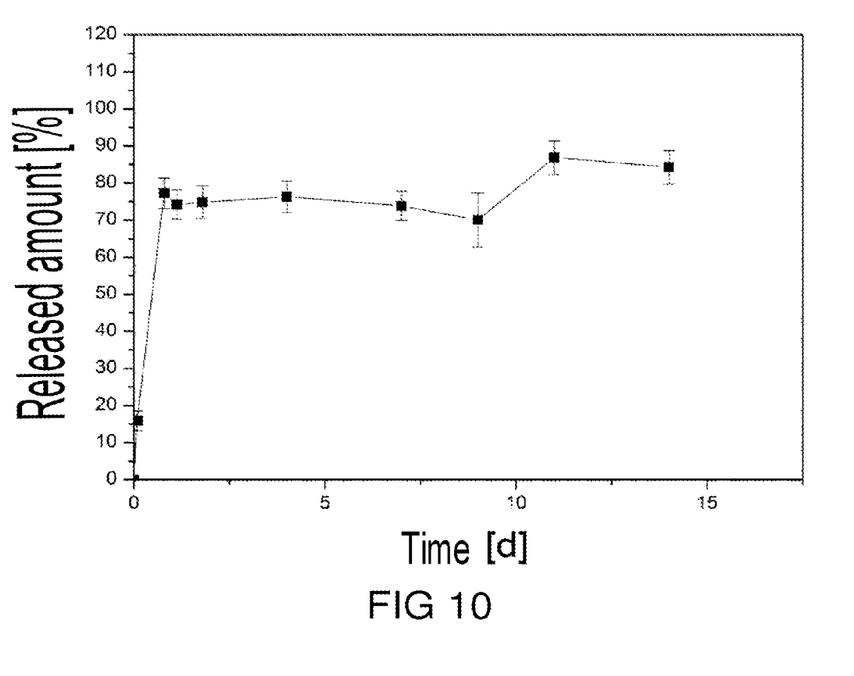
FIG. 10 shows one in-vitro release kinetic of gonadorelin [6-D-Phe] from a matrix composed of glycerol tristearate+40% CSA.

The following matrices were employed as dimensionally stable matrices:

| FIG. | Matrix |
|---|---|
| FIG. 2 | Glycerol tripalmitate + 10% glycerol monostearate (GMS) |
| FIG. 3 | Glycerol tripalmitate + 20% GMS |
| FIG. 4 | Glycerol tristearate + 10% GMS |
| FIG. 5 | Glycerol tristearate + 20% GMS |
| FIG. 6 | Glycerol tristearate + 40% GMS |
| FIG. 7 | Glycerol tripalmitate + 10% cetyl stearyl alcohol (CSA) |
| FIG. 8 | Glycerol tripalmitate + 20% CSA |
| FIG. 9 | Glycerol tripalmitate + 60% CSA |
| FIG. 10 | Glycerol tristearate + 40% CSA |

Figure 11:
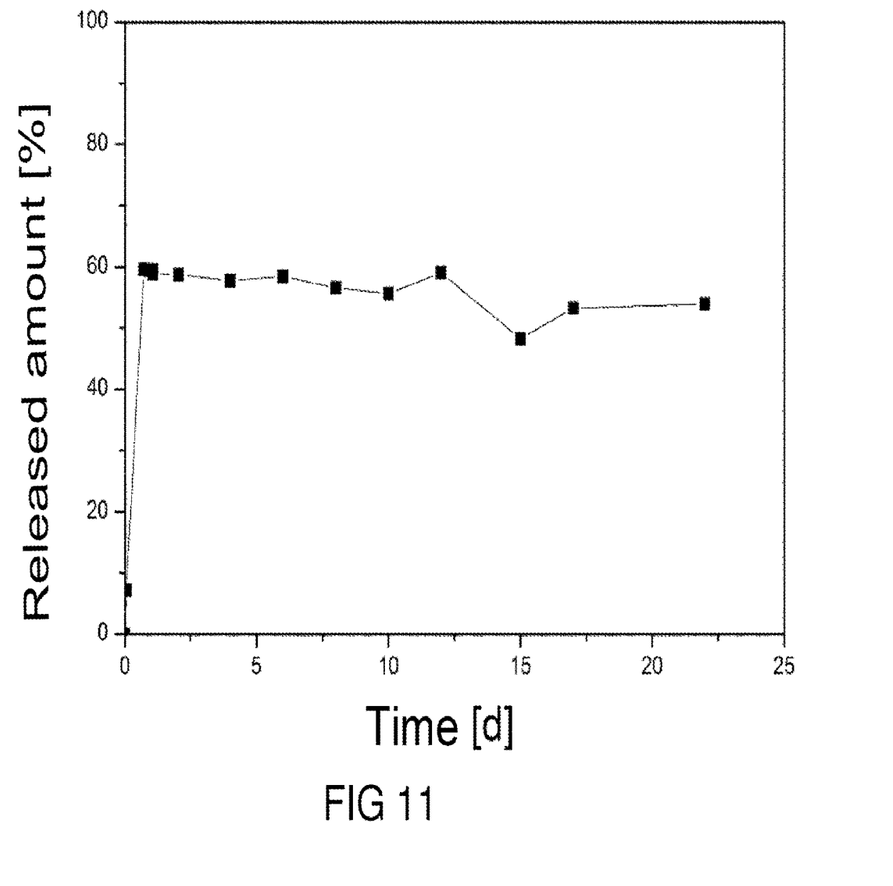
FIG. 11 shows one in-vitro release kinetic of gonadorelin [6-D-Phe] from a matrix composed of glycerol monostearate.

FIG. 11 shows the release kinetics of a comparative example in which the matrix consists not of one of the claimed substances, but only of a monoglyceride, in this case glycerol monostearate. The release kinetics were obtained in the same manner as the release kinetics shown in FIGS. 2 to 10.

It can be seen from FIG. 11 that the release only took place within one day. Thereafter, the amount released remained at the level which had originally been released; no further release took place over the period of up to 22 days. Thus, this release kinetic, which relates to a non-inventive matrix, differs markedly from the release kinetics which were obtained with the matrices according to the invention. This is because in each case a delayed release of the active substance may be observed here over a period of up to 15, or up to 22, days.

We claim:

1. A veterinary pharmaceutical composition, comprising at least one active veterinary pharmaceutical substance which is selected among gonadorelin and gonadorelin analogs as well as salts of gonadorelin and of the gonadorelin analogs, wherein the composition includes a liposome-free matrix which delays the release of the active veterinary pharmaceutical substance from the composition, which matrix includes a basic material which is selected from the group consisting of glycerol tripalmitate, glycerol tristearate, and mixtures of these substances, the veterinary pharmaceutical composition comprising no biodegradable polymer.

2. The veterinary pharmaceutical composition as claimed in claim 1, wherein the active veterinary pharmaceutical substance is only released over a period of up to 25 days after the application of the veterinary pharmaceutical composition.

3. The veterinary pharmaceutical composition as claimed in claim 1, wherein the release of the active veterinary pharmaceutical substance drops suddenly below a veterinary pharmaceutically active dosage at the end of the release period.

4. The veterinary pharmaceutical composition as claimed in claim 1, further comprising gonadorelin[6-D-Phe] as the active veterinary pharmaceutical substance.

5. The veterinary pharmaceutical composition as claimed in claim 1, wherein the matrix includes an emulsifier.

6. The veterinary pharmaceutical composition as claimed in claim 5, wherein the emulsifier is selected from the group consisting of monoglycerides, diglycerides, partial glycerides, sorbitan fatty acid esters, fatty alcohols, lecithin, cholesterol, esters of polyethylene glycol and an oil, and mixtures of these substances.

7. The veterinary pharmaceutical composition as claimed in claim 6, wherein the emulsifier is selected from the group consisting of glycerol monostearate, glycerol monopalmitate, glycerol distearate, glycerol dimyristate, glycerol dipalmitate, glycerol monocaprylate, glycerol stearate citrate, glycerol stearate, glycerol monocaprylocaprate type I, glycerol cocoate, glycerol monooleate, sorbitan trioleate, sorbitan monolaurate, sorbitan monopalmitate, sorbitan monostearate, sorbitan tristearate, sorbitan monooleate, sorbitan sesquioleate, cetylstearyl alcohol, cetyl alcohol, stearyl alcohol, myristyl alcohol, behenyl alcohol, lecithin, cholesterol, phosphatidylcholine, esterified phosphatidylcholine, (1,2-dimyristoyl-sn-glycero-3-phosphocholine), (1-palmitoyl-2-oleoyl-sn-glycero-3-phosphocholine), sorbitan monolaurate, sorbitan monopalmitate, sorbitan monostearate, sorbitan tristearate, sorbitan monooleate, sorbitan sesquioleate, sorbitan trioleate, polyoxyethylene(20) sorbitan monolaurate, polyoxyethylene(20) sorbitan monopalmitate, polyoxyethylene(20) sorbitan monostearate, polyoxyethylene(20) sorbitan tristearate, polyoxyethylene(20) sorbitan monooleate, polyoxyethylene(20) sorbitan trioleate, macrogol glycerol ricinoleate (35), macrogol glycerol ricinoleate (40), PEG-6-almond kernel oil, PEG-6-almond oil, PEG-6-groundnut oil, PEG-6-olive oil, PEG-6-corn oil, PEG-6-palm kernel oil, PEG-6-hydrogenated palm kernel oil and PEG-8-corn oil, and mixtures of these substances.

8. The veterinary pharmaceutical composition as claimed in claim 1, wherein the veterinary pharmaceutical substance is configured as a one-phase solution or as a dispersion with a one-phase dispersion medium.

9. The veterinary pharmaceutical composition as claimed in claim 1, wherein the active veterinary pharmaceutical substance is present in micro encapsulated form.

10. The veterinary pharmaceutical composition as claimed in claim 1, wherein the active veterinary pharmaceutical substance is released at a dosage of 10 to 1000 µg per 24 hours.

11. The veterinary pharmaceutical composition as claimed in claim 1, wherein the veterinary pharmaceutical composition is present as a suspension.

12. The veterinary pharmaceutical composition as claimed in claim 1, wherein the veterinary pharmaceutical composition is present as a dimensionally stable formulation.

13. The veterinary pharmaceutical composition as claimed in claim 1, wherein the veterinary pharmaceutical composition comprises at least one additive which differs from the matrix and which is selected from the group consisting of porosity agents, lipids, phospholipids, thickeners and partial glycerides.

14. A method for using the veterinary pharmaceutical composition as claimed in claim 1 in the control of the sexual cycle of female animals.

15. The method as claimed in claim 14, wherein the animals are gilts.

16. The veterinary pharmaceutical composition as claimed in claim 2, wherein the release of the active veterinary pharmaceutical substance drops suddenly below a veterinary pharmaceutically active dosage at the end of the release period.

17. The veterinary pharmaceutical composition as claimed in claim 2, further comprising gonadorelin[6-D-Phe] as the active veterinary pharmaceutical substance.

* * * * *